United States Patent [19]

Barnett et al.

[11] Patent Number: 4,654,305

[45] Date of Patent: Mar. 31, 1987

[54] MULTIPHASE REACTOR SYSTEMS BASED ON FOAMS FOR SIMULTANEOUS GROWTH AND SEPARATION OF PRODUCTS

[75] Inventors: Stanley M. Barnett, Wakefield; Kenneth A. Bradley, Westerly, both of R.I.

[73] Assignee: The Board of Governors for Higher Education State of Rhode Island and Providence Plantations, Providence, R.I.

[21] Appl. No.: 792,637

[22] Filed: Oct. 28, 1985

Related U.S. Application Data

[63] Continuation of Ser. No. 296,229, Aug. 25, 1981, abandoned.

[51] Int. Cl.[4] ............................................. C12N 1/34
[52] U.S. Cl. .................................................. 435/246
[58] Field of Search ................ 209/166; 210/703–705, 210/708; 435/246

[56] References Cited

U.S. PATENT DOCUMENTS 3,900,420  8/1975  Sebba ............................. 435/246 X
4,041,180  8/1977  Wilson ........................... 435/246 X Primary Examiner—Ferris H. Lander
Attorney, Agent, or Firm—Thompson, Gauthier, Samuels, Stevens & Kehoe

[57] ABSTRACT

A nutrient gas is introduced into a liquid nutrient formulation. The resulting nutrient media is a foam. The bubble size of the gas phase is between 0.1 to 200 microns and the foam is 40–80% voids.

8 Claims, 1 Drawing Figure

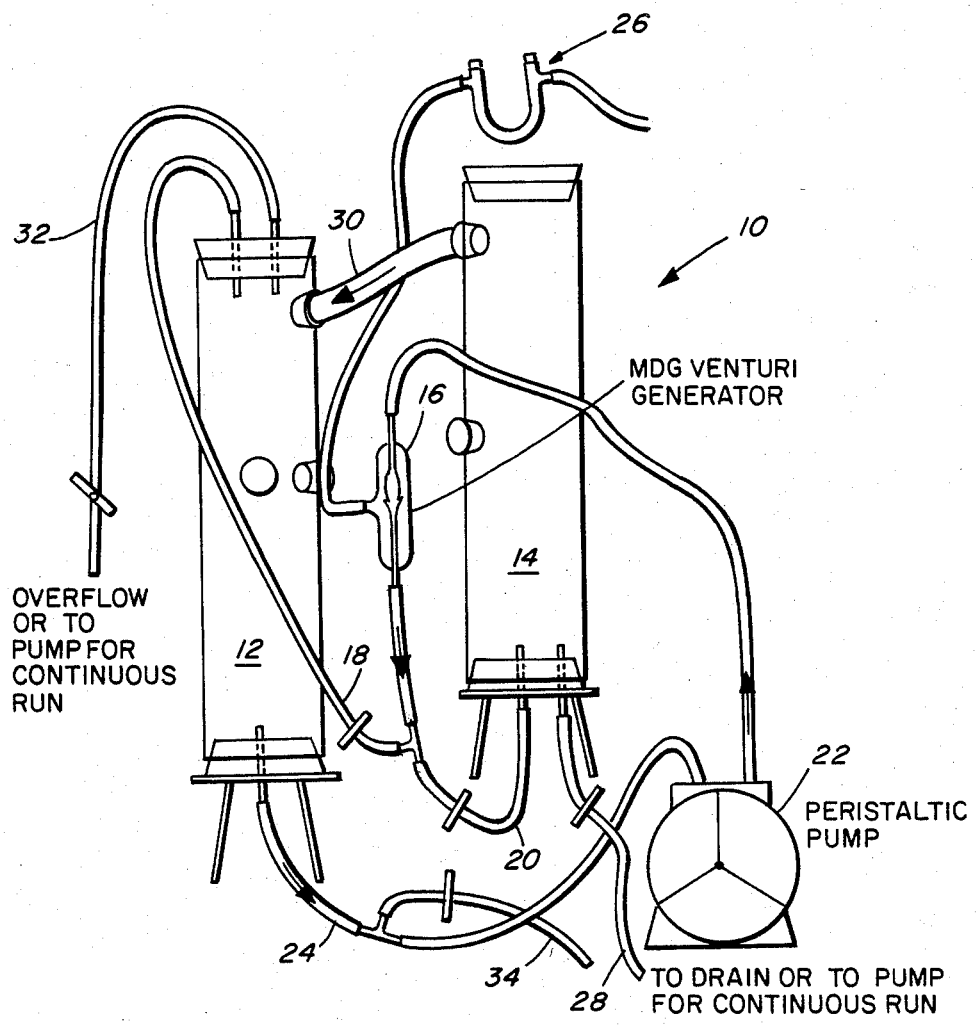

MULTIPHASE REACTOR SYSTEMS BASED ON FOAMS FOR SIMULTANEOUS GROWTH AND SEPARATION OF PRODUCTS

This is a continuation of copending application Ser. No. 296,229 filed on Aug. 25, 1981 and now abandoned.

BACKGROUND AND BRIEF SUMMARY OF THE INVENTION

Many fermentations are carried out in batch or continuously stirred tank reactors which are supplied with air or oxygen by means of spargers. Increased oxygen transfer rates are usually obtained by breaking up the bubbles and distributing them by means of an impeller. Bubble sizes are typically one millimeter or larger. Organism growth or product formation is often hampered by the formation of stagnant layers of foam that form on the top of the fermentation broth. See for example U.S. Pat. No. 3,846,246, Midorikawa et al. Typically, mass transfer in these systems is at the expense of energy.

Tower fermentors are also commonly used with large quantities of air sparged from the bottom of the apparatus to provide both aeration, mixing and in some cases, improved heat transfer. The fermentor may be divided into two parts, a riser and a downcomer as in an air lift fermentor.

Separation procedures for the fermentation products, cells and/or chemicals, usually involve one or more of the following unit operations: centrifugation, extraction, distillation, filtration, ultrafiltration, crystallization and flocculation. Flotation is uncommon and usually considered a nuisance. It has been tried for the separation of proteins, including enzymes, and for the removal of microorganisms.

The present invention is broadly directed to a method of fermentation wherein the fermentation media is a stable nutrient media dispersion comprising a phase of microgas bubbles and a liquid phase. The microgas bubbles or bubble foam per se are known in the art; see U.S. Pat. No. 3,900,420 Sebba; however, this reference does not teach the use of the microgas bubbles as a part of the nutrient broth per se.

In one aspect of the invention, a fine dispersion (about $10^{-5}$ micron diameter bubbles) of a gas in a nutrient broth is provided. The dispersion provides an extremely large surface area per reactor volume for improved oxygen transfer to the microorganism, increased growth surfaces for the organisms, if needed, and a devide for flotation of fermentation products such as cells or the like; or a product for separations within the fermentor. Moreover, the invention makes use of the bubble foam, usually considered a nuisance or used merely for separations. The invention has lower air and power requirements than prior art systems such as stirred tank or tower fermenters. The foam can be used to harvest the microorganisms from the broth or for selective separation of products such as enzymes, antibiotics, proteins, cells and/or vitamins. The bubbles can be used as a catalyst by binding either microorganisms, enzymes or traditional catalysts to the surface. The advantages of the invention are increased oxygen transfer (or nutrient gas transfer) due to the very small bubble sizes, the coupling of the organism and/or substrate and catalyst to the bubble surface and simultaneous mixing, aeration and product and/or cell separation.

Broadly, the invention includes a method of fermentation which includes introducing a nutrient gas into a liquid nutrient formulation to create a stable nutrient media, to effect fermentation, comprising a liquid phase and a gaseous phase, the gaseous phase dispersed throughout the liquid phase to provide a foam-like medium. The bubble size of the gaseous phase is between about 0.1 to 200 microns and about 40–80% voids of the entire dispersion. Subsequently the fermentation products are separated from the dispersion.

BRIEF DESCRIPTION OF THE DRAWINGS

The drawing is a schematic of a fermentor used in the preferred embodiment of the invention.

DESCRIPTION OF THE PREFERRED EMBODIMENT

Referring to the drawing, a fermentor 10 consists of dual towers 12 and 14, tower 12 being a reservoir tower or downcomer; and tower 14 being a separations column or riser. A foam generator 16 is connected to both towers 12 and 14 via conduits 18 and 20, respectively. Each of these conduits includes valves. Upstream of the generator 16 is a peristaltic pump 22. A conduit 24 connects the bottoms of the reservoir tower 12 to the upstream side of the pump 22. A nutrient gas flows through a filter 24 and then into the generator 16. The column 14 includes conduit 28 which functions as a drain.

Transfer of the fermentation media between columns is via a conduit 30. The removal of the fermentation products from the columns may be either bypassing from conduit 30 or from the conduit 32 secured to the upper portion of the column 12.

Initially, liquid nutrient is placed in both columns 12 and 14. The valve on conduit 18 is open; the conduit on line 20 is open; the valve on conduit 28 is closed; and the valve on conduit 32 (drain) is closed.

The pump 22 is actuated and air flows through the generator 16 and to the columns 12 and 14. The liquid nutrient in both columns quickly becomes a foam mass of micron-size bubbles with about a 60–70% void volume. The valve on conduit 18 is closed and the valves on the drain conduit 28 and the overflow conduit 32 are opened. If operating a continuous operation rather than a batch operation additional liquid nutrient may be introduced through conduit 34.

Bottoms accumulate in the column 14, i.e. some of the original liquid nutrient of that liquid which cannot be supported by the foam mass. The bottoms are continuously drained off as they overflow the upper end of the drain line, (Weir).

The foam moves upwardly and through the column 14, through the conduit 30 and into the column 12. A portion of the foam is removed via conduit 32. The remainder of the foam is withdrawn through the bottom of the column 12, recycled through the pump 22, through the generator 16 and back into the column 14.

The venturi can be replaced by a cyclone or other suitable device. Generally a surfactant is used such as a synthetic surfactant or a surfactant can be used produced by the organism itself, a biosurfactant, or by other natural methods. Suitable surfactants include sodium dodecylsufate, sodium dodecylbenzene sulfonate and ethylhexadecyldimethylammonium bromide. The bubble foam having high void volumes, 50–70%, are non-Newtonian. The size of the bubbles may range from 0.1 microns to 200 microns. In the examples that follow, the average length mean diameter (LMD) of the bubbles is believed to be about 50 microns, with approximately 50% of the bubbles produced in the foam mass in both towers being approximately 50 microns in diameter ±10%. The distribution of bubbles size LMD, ranges from the largest bubble size being 100 microns and to the lowest bubble size being approximately 0.1 micron.

The invention solves the following problems which plague either one or the other or all of the traditional methods of fermentation. First, the high mass transfer requirements are greatly aided by the large amount of surface area created by the 1-100 micron diameter bubbles coupled with high holdups about 60-70%. Increased oxygen or other fluid liquid or gas nutrient transfer, removal of carbon dioxide, alcohol, ammonia or other gaseous waste products is achieved. Mixing is provided by bubble turbulence or by the passage of the foam through the generator. Separation of cells can be carried out without an additional step, by having them carried off by the foam. This operation saves separate centrifugation or filtration. Similarly, certain products, such as enzymes, can be removed by making use of their surface active properties.

The amount of air required for an aerobic fermentation, expressed as v/v/m, can be on the order of $10^4$ times less than a traditional fermentor, calculated power comsumption is also less, heat removal is easier, growth of surface loving organisms is promited which is useful for film formers, and higher holdups and an even distribution of bubbles throughout the fermentor is an advantage over tower fermentors, especially the airlift type.

EXAMPLE I

The following example was carried out in the fermentor shown in FIG. 1. *Saccaharomyces cerevisiae* ATTC was grown on a nutrient broth consisting of 29.29 g/l dextrose, 0.365 g/l $KH_2PO_4$. 4.84 g/l $(NH_4)_2SO_4$, 0.053 g/l $CaCl_2 \cdot 2H_2O$ and 0.845 g/l yeast extract in distilled water. A non-ionic surfactant, Tween 20, was added at the 250 ppm level. About 800 ml of an inoculant culture, grown through two shake flask cultures from agar slants, was added to 5 l of the broth in the fermentor. Air flows to the fermentor via the generator was 0.3 SCFH. Ph was maintained at 5 by addition of conc. $NH_4OH$. Comparison of a batch fermentation using the invention with that in a stirred tank reactor produced the following results:

| | Invention | Stirred tank reactor |
|---|---|---|
| Specific growth rate, $hr^{-1}$ | 0.31 | 0.26 |
| Air flow l/l/m | 0.017 | 1-2 |
| Relative power input per unit volume | 3.9 | 55.2 |

The foam removed is allowed to collapse and the cells are collected in a conventional manner.

EXAMPLE II

The example 1 was repeated in a continuous mode with cell harvest. The same data was achieved. Fresh nutrient solution was added at the rate of 500/ml/hr and fermentation broth removed at the same rate.

EXAMPLE III

A fermentation without surfactant was tried. It was found that certain organisms produce a surfactant suitable for foam production. *S. cerevisiae* was such an organism but the best results were obtained with additional synthetic surfactant.

We have used 1-100 micron size bubbles in a modified airlift fermentor. The fermentation broth was nearly all bubbles and both the bubble foam and microorganisms were pumped through the generator. The results shown above are an improvement over traditional fermentation procedures. The invention can be used for the following systems; aerobic or anerobic growth of yeast, fungi, bacteria, algae, and other cells. This group includes: yeast growth for protein or enzyme production; production of alcohol from soluble or insoluble substrates with or without cellulases or an amylases added; growth of yeast or bacteria on hydrocarbons for hydrocarbon breakdown, fatty acid or biosurfactant production; growth of algae on carbon dioxide; and production of biopolymers or gums by various organisms.

The invention can be used as an enzyme reactor without the microorganisms. The enzymes, such as 3-galactosidase or 3-glucosidase, can be bound to the surface of the foam by traditional crosslinking or adsorption procedures.

The bubbles can consist of oxygen or any other nutrient gas including carbon dioxide and methane. Gas or vapor exchange can be carried out to remove products such as alcohol and carbon dioxide. Controlled levels of oxygen and carbon dioxide can be maintained for special purposes such as alcohol production under microaerobic conditions.

The foam can be used to remove cells, enzymes, antibiotics or other products by simple foam filtration, adsorption, ion exchange, affinity chromatography or other methods. The surfactant(s) can be modified to carry out these tasks. The foam can be used to harvest biosurfactants.

Non-surfactant products can be removed from a quiescent area at the bottom of the riser.

The bubble foam can be made by the venturi device shown, a cyclone or other suitable devices including depressurization and electrochemical methods. Packed bed generators are also feasible.

Having described our invention, what we now claim is:

1. A method of fermentation which includes:
   (a) introducing a nutrient gas into a liquid nutrient formulation to create a stable nutrient media comprising both a liquid phase and a dispersed gaseous phase with high interfacial area, the gaseous phase dispersed throughout the liquid phase to provide a foam-like medium, the bubble size of the dispersed gaseous phase being between 0.1-200 microns and the void volume being between 40-80 percent;
   (b) maintaining the void volume between 40-80 percent while effecting fermentations to create fermentation products; and
   (c) collecting the fermentation products from the foam.

2. The method of claim 1 wherein the nutrient gas includes, oxygen, carbon dioxide, nitrogen and methane.

3. This method of claim 1 wherein the fermentation includes anerobic, aerobic and microaerobic processes.

4. The method of claim 1 wherein the collecting includes harvesting antibiotics, enzymes, proteins, cells and vitamins.

5. The method of claim 1 wherein the bubble size is from 0.1-50 microns.

6. The method of claim 1 wherein the void size of the foam is between 50-70%.

7. The method of claim 1 wherein the liquid nutrient formulation is in a first tower and which includes:
flowing the nutrient gas into the first tower to create the stable nutrient foam;
transfering the nutrient foam from the first column to a second column;
bypassing a portion of the foam transferred from the first column to the second column to harvest the fermentation products therefrom; and recycling at least a portion of the nutrient foam from the second column to the first column.

8. The method of claim 1 which includes:
collapsing the nutrient foam; and
collecting the fermentation products from the collasped foam.

* * * * *